United States Patent [19]

McGee et al.

[11] Patent Number: 5,585,343
[45] Date of Patent: Dec. 17, 1996

[54] LOW VOC PERFUME FORMULATIONS

[75] Inventors: Thomas McGee, Orangeburg, N.Y.; Saroja Narasimhan, Englewood; Caryl E. Yeager, Madison, both of N.J.

[73] Assignee: Givaudan-Roure Corporation, Clifton, N.J.

[21] Appl. No.: 306,071

[22] Filed: Sep. 19, 1994

Related U.S. Application Data

[63] Continuation-in-part of Ser. No. 145,873, Nov. 3, 1993, abandoned.

[51] Int. Cl.$^6$ .................................................. A61K 7/46
[52] U.S. Cl. ................................ 512/1; 512/2; 512/3
[58] Field of Search .................................. 512/1, 2, 3

[56] References Cited

U.S. PATENT DOCUMENTS

| | | | |
|---|---|---|---|
| 4,089,814 | 5/1978 | Schmolka | 512/3 |
| 4,146,499 | 3/1979 | Rosano | 252/186 |
| 4,268,498 | 5/1981 | Gedeon et al. | 424/59 |
| 4,797,272 | 6/1989 | Linn et al. | 424/59 |
| 4,810,690 | 3/1989 | Dumas | 512/2 |
| 5,079,227 | 1/1992 | Handjani et al. | 512/2 |
| 5,246,918 | 9/1993 | Behan et al. | 512/2 |
| 5,252,555 | 10/1993 | Dartnell et al. | 512/4 |
| 5,283,056 | 2/1994 | Chung et al. | 512/2 |

FOREIGN PATENT DOCUMENTS

| | | | |
|---|---|---|---|
| 261351 | 3/1988 | European Pat. Off. | 512/2 |
| 462605 | 12/1991 | European Pat. Off. | 512/4 |
| 516508 | 12/1992 | European Pat. Off. | 512/2 |
| 572080 | 12/1993 | European Pat. Off. | 512/2 |
| 571677 | 12/1993 | European Pat. Off. | 512/2 |
| 3304822 | of 0000 | Germany | 512/2 |
| 2639293 | 3/1978 | Germany | 512/2 |
| 2901068 | 7/1979 | Germany | 512/2 |
| 57-159707 | 3/1981 | Japan | 512/2 |
| 5-161698 | 6/1993 | Japan | 512/2 |
| 2230447 | 10/1990 | United Kingdom | 512/4 |

OTHER PUBLICATIONS

Blakeway (Perfumer & Flavorist, 18, Jan./Feb., p. 33, 1993).
Friberg et al., (Cosmetics & Toiletries, vol. 97, Jun. 1982).
Shinoda et al., (Microemulsions, Theory and Practice, ed., Leon Prince, Academic Press, 1977).

*Primary Examiner*—James H. Reamer
*Attorney, Agent, or Firm*—George W. Johnston; Catherine R. Smith; Mark E. Waddell

[57] ABSTRACT

Oil-in-water (O/W) and water-in-oil (W/O) microemulsions of fragrance product formulations are provided. The microemulsions are clear or at least translucent, sprayable, and non-sticky. Novel combinations of anionic surfactant components (a) and hydrophilic coactives (highly water soluble component (b) or a mixture of highly water soluble (b)(i) and less water soluble polar (b)(ii) components) are used to obtain fragrance product formulations that are free or substantially free of ethanol. The anionic surfactants have a hydrophilic-lipophilic balance ("HLB") modified by the use of classes of anionic surfactant components (a) and commercially available hydrophilic component coactives ((b) or mixture of (b)(i) and (b)(ii)), not previously recognized as effective in this type of system. Highly, preferably infinitely, water soluble coactives (b) as well as mixtures of highly, preferably infinitely, water soluble coactives (b)(i) with other less water soluble polar coactives (b)(ii), modify the HLB of anionic surfactants in such a way as to enable the formation of stable, clear microemulsions of fragrance product compositions. These compositions contain lower ratios of surfactant to oil than conventional nonionic (or ionic surfactants with lipophilic coactives) aqueous or alcohol free compositions. As such, the present fragrance compositions are sprayable and nonsticky.

22 Claims, No Drawings

LOW VOC PERFUME FORMULATIONS

This application is a continuation-in-part application of Ser. No. 08/145,873, filed Nov. 3, 1993, now abandoned.

FIELD OF THE INVENTION

This invention relates to the preparation of low VOC, aqueous or low ethanolic, clear, sprayable, non-sticky fragrance formulations containing conventional aroma chemicals at levels of 0.5% to 40%, preferably 1% to 30%, which are in a new microemulsion composition.

BACKGROUND

The need to have cosmetically acceptable, sprayable, low or zero ethanol fragrance formulations is due to concerns about volatile organic compounds (VOC), which are claimed to produce ground level ozone under certain extreme weather conditions. Fragrances at levels of 0.5% or above are most commonly solubilized with ethanol. However, ethanol is considered to be a VOC under many current and pending regulations.

The task of producing a low or zero ethanol formulation, which resembles an ethanolic fragrance formulation in all aspects, is difficult and the problem increases as the level of fragrance increases. Low ethanol formulations are formulations which are substantially free of ethanol.

Blakeway (Perfumer & Flavorist, 18, Jan/Feb., p. 23, 1993) reviews water based perfumes. He focuses on the use of solubilizers, in particular, non-ionic surface active agents. The formulations given by Blakeway require high ratios of surfactant to perfume oil which leave a sticky feeling on the skin and can produce unwanted levels of product foaming. At page 24, column 1, paragraph 3 Blakeway indicates that perfume compositions having 10% or greater perfume oils give viscosities of 20–50 cps which can not be used in conventional pump sprays. Also, higher concentrations of surfactants needed for the higher concentration of perfume oils gives the microemulsions their tendency to foam in the bottle. At page 26 under the heading "pump spray" this document teaches that a viscosity of less than about 15 cps (at 20° C.) of a water based perfume is needed for pump spray applications.

Microemulsions represent one approach to producing clear, transparent products. These are dispersions of oil-in-water or water-in-oil systems in which the droplet size is small enough to permit light to pass through. U.S. Pat. No. 4,146,499 shows how oil-in-water microemulsions can be prepared using a primary surfactant with a hydrophilic-lipophilic balance ("HLB") not substantially less than required to make it soluble in the oil phase. A second surfactant having a higher HLB than the primary surfactant, is used to convert the dispersion to a microemulsion. Non-ethanol fragrances produced by this method are viscous and translucent even at low, e.g., 1%, fragrance levels.

Linn et al., discloses in U.S. Pat. No. 4,797,272, water-in-oil microemulsions for cosmetic uses containing moisturizing agents or sunscreens. These microemulsions are formulated with non-ionic surfactants and produce products comparable to typical skin care creams and lotions and are not at all similar to perfume and cologne formulations. While some may be flowable, none is sprayable and non-tacky which are fundamental requirements for replacement of ethanolic perfume products.

U.S. Pat. No. 5,252,555 to Dartnell et al relates to microemulsions containing a perfuming concentrate from 5 to 50% by weight, and a surfactant based on polyethylene glycol, a first co-surfactant based on polyglycerol and a second co-surfactant based on ether phosphate. Thus the compositions contain a very large amount of surfactant. Moreover, the surfactants utilized in these compositions are non-ionic surfactants.

European Patent 516508 corresponds to U.S. Pat. No. 5,252,555 to Dartnell. The U.S. patent English version is discussed above.

Microemulsions in which the primary surfactant is anionic have been studied. However, coactives are required to modify the HLB and allow the formation of microemulsions. This prior art (as discussed by Friberg, et al, Cosmetics & Toiletries, Vol. 97, June 1982 and Kozo Shinoda and Hironobu Kunieda in Microemulsions, Theory and Practice, ed., Leon Prince, Academic Press, 1977) disclosed that a lipophilic coactive, such as a medium chain length alcohol, is required to reduce the HLB into the range required for microemulsion formation. Use of these lipophilic coactives as the sole coactive at the required levels for microemulsions, is not desirable for perfume compositions because they typically have unpleasant odors and frequently have undesirable skin feel characteristics.

U.S. Pat. No. 4,146,499 to Rosano teaches the use of two surfactants to produce microemulsions, but does not produce sprayable compositions at higher perfume oil concentrations. The non-ethanol fragrances produced by this method are viscous and translucent even at low, for example 1%, fragrance levels. The language in this patent is very broad as regards a first surfactant which is lipophilic and a second surfactant which is hydrophilic.

European Patent 571,677 relates to clear oil-in-water microemulsions comprising a perfume oil, an aqueous phase and a surfactant. The microemulsions comprise less than 25%, preferably less than 5% alcohol. The surfactants may be either ionic or non-ionic. The co-surfactants are present in less than 50% by weight of the total surfactant as described on page 5, lines 33–38. This patent does not describe an anionic surfactant at a concentration lower than a coactive. Further, the European patent application does not describe any microemulsions comprising a perfume oil, an anionic surfactant in combination with a hydrophilic coactive solvent, wherein the hydrophilic coactive is in higher concentration than the anionic surfactant.

European Patent 572,080 to Behan et al concerns aqueous perfume oil micro-emulsions. The text of the patent application is similar to the text of European Patent 571,677. Example 3 shows a combination of primary nonionic surfactants plus cosurfactants at least one of the cosurfactants being anionic. The micro-emulsions are characterized as being fine fragrances or air fresheners. The claim states that the weight ratio of perfume oil to total surfactant is between 0.85 and 2.5, which stated in the reverse is that the ratio of total surfactant to perfume oil is from about 0.4 to about 1.2.

Other background art is discussed below.

Japanese Kokai 161698/1993 to ST Chemicals Limited relates to water soluble solvents and water in combination with perfume oils. Accordingly this document does not relate to perfume oils micro-emulsified via an anionic surfactant in combination with a hydrophilic coactive.

U.S. Pat. No. 5,283,056 to Chung et al relates to mouthwash compositions comprising water, a flavor or fragrance oil, and one or more surfactants. As described on page 4, lines 50–55 the mouthwash compositions have a viscosity ranging from about 70 to about 18,000 cps.

Japanese Patent 57-159707 relates to solubilizing perfume oils in water or an aqueous medium. A mono- or poly-hydric alcohol is used in combination with a surfactant to solublize the perfume oils.

U.S. Pat. No. 4,089,814 to Schmolka relates to roll-on perfume compositions comprising 25–40 parts of an alcohol and block copolymers as well as water. A requirement for such compositions is that the compositions are viscous, clear and stable perfumes. Clearly such viscous compositions are not sprayable compositions. Further there is no mention of an anionic surfactant in combination with a hydrophilic coactive.

EP 261,351 to Blakeway relates to aqueous or aqueous-alcoholic solutions of fat soluble perfume oil containing an alkylene oxide polymer and a nonionic emulsifier. Thus document does not describe sprayable perfumes utilizing an anionic surfactant in combination with a hydrophilic coactive.

U.S. Pat. No. 4,268,498 to Gedeon et al relates to solid clear cosmetic sticks. Thus, sprayable compositions are not described. Although the compositions are described as clear they are also viscous because they are in a solid stick form.

German Patent 2901068 relates to deodorant compositions. The composition is a clear solution comprising a large amount of an anionic surfactant.

German Patent 3304822 relates to an odorant composition containing hexaalkyl-cyclo-trisiloxane perfume vehicles which dissolve a perfume and sublimate into the environment carrying the perfume into the air. Other volatile additives can be included to reduce the sublimation rate. Therefore, this document does not disclose a combination of an anionic surfactant and a coactive. The carrier agent is non-ionic.

U.S. Pat. No. 5,079,227 to Handjani et al relates to perfume compositions, with an aqueous phase, having a high concentration of perfume contained within nonionic lipid "vesicles." The lipid vesicles are derived from a linear or branched polyglycerol. Such lipid vesicle compositions are distinguished from oil-in-water or water-in-oil emulsions by Handjani et al in their discussion of background art. Further, the examples on pages 4–6 of Handjani et al refer to the compositions as compositions having the appearance of a cream.

U.S. Pat. No. 4,810,690 to Dumas relates to non-flammable homogeneous liquid air freshener compositions with an organic solvent base, which are not microemulsions of perfume oils.

UK Patent 2,230,447 relates to solublized air freshener compositions, rather than to microemulsified perfume compositions. A primary alcohol is used to solubilize the perfume oil in the described compositions. A secondary low volatility solvent, such as a glycol ether is used to slow the evaporation of the alcohol solvent. Thus the mechanism is not the formation of a clear microemulsion, but rather a homogeneous solution is formed.

SUMMARY OF THE INVENTION

This present invention provides oil-in-water (O/W) and water-in-oil (W/O) microemulsion fragrance product formulations which are (clear or at least translucent), sprayable, and non-sticky. In accordance with the invention, novel combinations of anionic surfactants and hydrophilic solvent coactives are used to obtain fragrance product formulations that are free or substantially free of ethanol. More particularly, the invention relates to the use of anionic surfactants having an HLB which has been modified by the use of classes of (hydrophilic solvents) coactives not previously recognized as effective in this type of system.

Surprisingly, it has been found that instead of lipophilic coactives, certain hydrophilic highly, preferably infinitely, water soluble coactives (hydrophilic solvents) as well as mixtures of highly, preferably infinitely, water soluble solvent coactives with other less water soluble polar solvent coactives, modify the HLB of anionic surfactants. The HLB is sufficiently modified by the highly water-soluble hydrophilic coactives, or mixture of highly water-soluble hydrophilic coactives and less water-soluble polar coactives, that stable, clear microemulsions of fragrance product compositions are able to be formed.

These compositions contain lower ratios of surfactant to oil than conventional nonionic aqueous or alcohol free compositions. Further, the amount by weight of hydrophilic solvent coactive, or mixture of coactives, by weight is greater than the amount of anionic surfactant in these fragrance compositions. As such, the fragrance compositions in accordance with the invention are sprayable and non-sticky.

The perfume materials are generally present in said formulations in amounts within the range of about 0.5% to 40%, preferably 1.0 to 30% by weight of the final formulation.

The primary surfactant, which is anionic, is typically present in levels of about 1.0% to 40%, preferably 2.0% to 20% by weight of the final formulation.

The hydrophilic coactive solvent is present in a level that exceeds that of the anionic surfactant. Typically, the hydrophilic coactive solvent is in the range of about 1.5% to 55%, preferably 6.0% to 45% by weight of the final formulation.

DETAILED DESCRIPTION

In the present invention, different levels of fragrance material are solubilized by a combination of an anionic component (a) and at least one hydrophilic component (b), wherein (a) is an anionic surfactant or a combination of anionic surfactants, said surfactant or surfactants being selected from the group consisting of acyl glutamates, alkyl sulphates, alkali metal sulphates, ammonium sulphates, substituted ammonium alkyl sulphates, alkyl ether sulphates having 10 to 30 carbon atoms in the alkyl moiety and 1 to 50 ethylene oxide units, sulphosuccinates, alkyl sulphonates, alkyl oxyalkane sulphonates, alkyl aryl sulphonates, alkanoic acid, alkanoates, sodium alkanoate soaps wherein the fatty acid moiety contains 10 to 20 carbon atoms, potassium alkanoate soaps wherein the fatty acid moiety contains 10 to 20 carbon atoms, triethanolamine soaps wherein the fatty acid moiety contains 10 to 20 carbon atoms, and acyl isothionates, or a combination thereof; said anionic surfactants being capable of forming a dispersion of said fragrance oil, or mixture of oils, and (b) is a highly water soluble, or infinitely water soluble, hydrophilic coactive solvent or mixture of hydrophilic solvents, said hydrophilic solvent or mixture being capable of sufficiently modifying the hydrophilic-lipophilic balance of said anionic surfactant or mixture of surfactants in said dispersion to enable formation of stable and clear, or near clear microemulsions of said fragrance oil or mixture of oils in water, said hydrophilic solvent or at least one of said hydrophilic solvents, being selected from the group consisting of short branched-chain or straight-chain aliphatic glycols, short branched-chain or straight-chain aliphatic ether alcohols, and ethoxylated polysiloxanes;

wherein said hydrophilic component (b) is present at a higher concentration by weight than said anionic component (a) in said perfumery composition; and wherein said fragrance oil, or mixture of fragrance oils, in combination with said components (a) and (b) in said perfumery composition is/are microemulsified to clarity or near clarity in an aqueous solvent.

The resulting microemulsions, in addition to being stable and clear or near clear, are also sprayable.

The fragrance materials of the perfumery compositions according to the invention are odiferous materials, which may be of any natural and/or synthetic origin. Of particular interest are oil soluble perfume oils, which may or may not be in a mixture with water soluble perfume oils. The oil soluble perfume oils are natural, or nature-identical essential oils, such as orange oil, pine oil, peppermint oil, eucalyptus oil, lemon oil, clove leaf oil, cedarwood oil, bergamot oil, rosemary oil, patchouli oil, lavandin oil, spike oil, rose oil, vetiver oil, fennel oil, anise oil, thyme oil, germanium oil, lavender oil, menthol etc. The fragrance materials may also be synthetic oil soluble perfume oils, selected from the usual group consisting of hydrocarbons, alcohols, ketones, aldehydes, esters and polyene compounds, etc. Naturally, this term also encompasses any mixture of perfume oils described above, or perfume concentrates or bases with preferably non-ethanolic diluents.

Preferred anionic surfactants (a) are selected from the group consisting of acyl glutamates such as monosodium cocoyl glutamate, $C_{9-18}$ alkyl sulphates, sodium lauryl sulphate, sodium laureth sulphate, sodium dioctyl sulphosuccinate, sodium $C_{12-14}$ olefin sulphonate, sodium 2-methoxy-tridecanesulphonate, sodium dodecyl benzene sulphonate, potassium oleate, sodium caprylate, and sodium cocoyl isothionate, or a combination thereof. The acyl glutamates are preferably $C_{12}$ to $C_{15}$ acyl glutamates.

Preferred highly water soluble, or infinitely water soluble, hydrophilic solvents (b) are selected from the group consisting of ethylene glycol, propylene glycol, butylene glycol, dipropylene glycol, hexylene glycol, isoprene glycol, methyl methoxy butanol, ethylene glycol butyl ether, propylene glycol methyl ether, and dimethicone copolyol, or a combination thereof. A preferred dimethicone copolyol is Dow Corning 193™.

Specifically, the compositions contain, primarily anionic surfactants component (a) at 1–40%, preferably 2–20%; component (b) at 1.5–55%, preferably 6–45%; which solublize perfume oils at levels of 0.5–40%, preferably 1–30%. The remainder of the formulation may be water or water/ethanol wherein the ethanol is present in only a low concentration.

In another embodiment of perfumery compositions according to the invention, different levels of fragrance material are solubilized by a combination of an anionic component (a) and at least one hydrophilic component (b), wherein (a) is an anionic surfactant, or a combination of anionic surfactants, said surfactant or surfactants being selected from the group consisting of acyl glutamates, alkyl sulphates, alkali metal sulphates, ammonium sulphates, substituted ammonium alkyl sulphates, alkyl ether sulphates having 10 to 30 carbon atoms in the alkyl moiety and 1 to 50 ethylene oxide units, sulphosuccinates, alkyl sulphonates, alkyl oxyalkane sulphonates, alkyl aryl sulphonates, alkanoic acid, alkanoates, sodium alkanoate soaps wherein the fatty acid moiety contains 10 to 20 carbon atoms, potassium alkanoate soaps wherein the fatty acid moiety contains 10 to 20 carbon atoms, triethanolamine soaps wherein the fatty acid moiety contains 10 to 20 carbon atoms, and acyl isothionates, or a combination thereof; said anionic surfactants being capable of forming a dispersion of said fragrance oil, or mixture of oils, and (b) is a mixture of components (i) and (ii), wherein (i) is a highly water soluble solvent selected from the group consisting of short branched-chain or straight-chain aliphatic glycols, short branched-chain or straight-chain aliphatic ether alcohols, and ethoxylated polysiloxanes; and (ii) is a polar water soluble solvent selected from the group consisting of short branched-chain or straight-chain aliphatic alcohols, unsubstituted aromatic alcohols, aromatic alcohols substituted by a branched-chain or straight-chained alkyl group, aromatic ether alcohols, and dimethyl silicones terminated with hydroxyl groups;

said mixture of (i) and (ii) being capable of sufficiently modifying the hydrophilic-lipophilic balance of said anionic surfactant or mixture of surfactants in said dispersion to enable formation of stable and clear, or near clear micro-emulsions of said fragrance oil or mixture of oils in water;

wherein said hydrophilic component mixture (b) is present at a higher concentration by weight than said anionic component (a) in said perfumery composition; and wherein said fragrance oil or mixture of fragrance oils in combination with said components (a) and (b) in said perfumery composition are microemulsified to clarity or near clarity in an aqueous solvent.

The fragrance materials of the perfumery compositions according to the invention are odiferous materials, which may be of any natural and/or synthetic origin. Of particular interest are oil soluble perfume oils, which may or may not be in a mixture with water soluble perfume oils. The oil soluble perfume oils are natural, or nature-identical, essential oils such as orange oil, pine oil, peppermint oil, eucalyptus oil, lemon oil, clove leaf oil, cedarwood oil, bergamot oil, rosemary oil, patchouli oil, lavandin oil, spike oil, rose oil, vetiver oil, fennel oil, anise oil, thyme oil, germanium oil, lavender oil, menthol, and the like, or combinations thereof. The fragrance materials may also be synthetic oil soluble perfume oils, selected from the usual group consisting of hydrocarbons, alcohols, ketones, aldehydes, esters and polyene compounds, and the like, or combinations thereof. Naturally, this term also encompasses any mixture of perfume oils described above, or perfume concentrates or bases with preferably non-ethanolic diluents.

Preferred anionic surfactants (a) are selected from the group consisting of acyl glutamates such as monosodium cocoyl glutamate, C9–18 alkyl sulphates, sodium lauryl sulphate, sodium laureth sulphate, sodium dioctyl sulphosuccinate, sodium $C_{12-14}$ olefin sulphonate, sodium 2-methoxy-tridecanesulphonate, sodium dodecyl benzene sulphonate, potassium oleate, sodium caprylate, and sodium cocoyl isothionate, or combinations thereof.

Preferred highly water soluble, or infinitely water soluble, hydrophilic coactive solvents (i) are selected from the group consisting of ethylene glycol, propylene glycol, butylene glycol, dipropylene glycol, hexylene glycol, isoprene glycol, methyl methoxy butanol, ethylene glycol butyl ether, propylene glycol methyl ether, and dimethicone copolyol, or combinations thereof. A preferred dimethicone copolyol is Dow Corning 193™.

Preferred water soluble polar solvents (ii) are selected from the group consisting of hexanol, octanol, decanol, benzyl alcohol, phenyl ethyl alcohol, ethylene glycol monophenyl ether, and dimethiconol, or combinations thereof. Most preferred (ii) components are selected from the group consisting of aromatic components, e.g. benzyl alcohol, phenyl ethyl alcohol, and ethylene glycol monophenyl ether, the latter being especially preferred.

Specifically, the compositions contain, primarily anionic surfactants component (a) at 1–40%, preferably 2–20%; component (b) at 1.5–55%, preferably 6–45%; which solublize perfume oils at levels of 0.5–40%, preferably 1–30%. The remainder of the formulation may be water or water/ethanol wherein the ethanol is present in only a low, i.e. trace, concentration.

The anionic surfactants, or a combination of anionics, listed under component (a) are provided by way of example, but are not intended to be exhaustive of this class of anionic surfactants. Additional anionic surfactants which may be used are described in McCutcheon's Emulsifiers and Detergents, 1989, which is incorporated herein by reference. Some amphoteric surface active agents may also be present in the anionic surfactant component.

The listed highly, preferably infinitely, water soluble materials ((b) or (b)(i)), alone, or in combination, with less water soluble polar components (b)(ii), modify the HLB of the surfactant system to allow the formation of a clear microemulsion are merely non-exhaustive examples of a class of compounds. The (b), (b)(i), or (b)(ii) components, alone or in combination, may also function as antisticking and antifoaming agents.

Both the aqueous and oil phase of the microemulsion of perfumery materials may contain other ingredients such as emollients, silicones (e.g., polydimethyl siloxane and poly phenyl methyl siloxane), preservatives, vitamins, UV absorbers, buffers, colorants, opacifiers, or other ingredients known to those skilled in the art of formulating cosmetic products.

In the present invention it has been found that the use of anionics in combination with a greater quantity by weight of coactive hydrophilic component(s) having high water solubility, or a mixture of highly and less highly water soluble coactives, reduces the amount of surfactant (a) required to solublize the perfume in a given formulation. For example, as low as 2% surfactant (a), in combination with coactives ((b) or (b)(i) and (b)(ii)), can solublize 1% fragrance oil in a water base cologne. Further, 7% surfactant (a) together with coactives ((b) or (b)(i) and (b)(ii)) can solublize 40% of fragrance oil, or oils, in a perfume formulation.

Furthermore, the microemulsion compositions of the present invention provide superior skin feel and are sprayable as compared to compositions prepared with nonionic systems, or with ionic systems utilizing lipophilic coactives to modify the HLB.

These compositions may be used under warm, humid conditions in summer or under cold, dry conditions in winter. While stability is important from an esthetic point of view, the use of anionics helps to increase the operable range of microemulsions of the present invention.

In addition, since these formulations contain water, commercially available surfactant components (a) and commercially available hydrophilic component coactives ((b) or (b)(i) and (b)(ii)), they can be produced in a cost effective manner.

All examples which follow contain conventional perfumes consisting of natural and synthetic ingredients. Perfume concentrate C is a fragrance which is used in small amount in an after shower body splash. Perfume concentrates BB, E, R and V are used in a men's cologne. Perfume concentrates G, J, S and SA are used in a women's cologne.

Preparation of the novel formulations is conveniently effected by mixing the perfume concentrate with the coactive(s), preferably at room temperature, until a homogeneous mixture results and then adding the surfactant(s), with mixing until uniform. The resulting premix is titrated with water under vigorous stirring.

The following examples demonstrate the application of the present invention in a given formulation where relatively lower ratios of surfactant (a) compared to nonionic formulas are effective using a single highly soluble coactive component (b) or a combination thereof. All values are given in weight percent. Each of the resulting compositions was sprayable, non-sticky and clear. It is also possible to include emollients or other typical cosmetic ingredients for consumer appeal.

EXAMPLE 1

|  | A | B |
| --- | --- | --- |
| Perfume C | 1.0 | 1.0 |
| Sodium Lauryl Sulfate | 3.0 | 2.0 |
| Dipropylene glycol | 6.0 | — |
| Dimethicone copolyol | — | 6.0 |
| Water to | 100 | 100 |

EXAMPLE 2

| Perfume J | 37.5 |
| --- | --- |
| Sodium dioctyl sulphosuccinate | 7.0 |
| Dipropylene glycol | 18.75 |
| Methyl methoxy butanol | 18.75 |
| Water to | 100.0 |

The following examples demonstrate formulations at multiple levels using mixtures of highly water soluble (i) and less water soluble (ii) coactives.

EXAMPLE 3

|  | A | B | C | D |
| --- | --- | --- | --- | --- |
| Perfume G | 5.0 | 8.0 | 12.0 | 18.0 |
| Sodium lauryl sulphate | 7.0 | 6.0 | 7.0 | 6.0 |
| Propylene glycol | 7.5 | 20.0 | 18.0 | 20.0 |
| Ethylene glycol monophenyl ether | 7.5 | 20.0 | 18.0 | 20.0 |
| Poly dimethyl siloxane | 2.0 | 1.0 | 1.0 | 2.0 |
| Water to | 100.0 | 100.0 | 100.0 | 100.0 |

In the above examples it can be seen that increasing levels of perfume can be solubilized with relatively low ratios of surfactant (a) to perfume by increasing the coactive component (b). Further formulations using mixtures of highly water soluble (i) and polar, less water soluble (b) coactive components are demonstrated below.

EXAMPLE 4

| | |
|---|---|
| Perfume E | 4.0 |
| Sodium cocoyl isothionate | 4.0 |
| Propylene glycol | 25.0 |
| Ethylene glycol monophenyl ether | 20.0 |
| Water to | 100.0 |

EXAMPLE 5

| | |
|---|---|
| Perfume R | 15.0 |
| Sodium caprylate | 6.0 |
| Dipropylene glycol | 47.0 |
| Decyl alcohol | 7.0 |
| Polyphenyl methyl siloxane | 1.0 |
| Water to | 100.0 |

EXAMPLE 6

| | |
|---|---|
| Perfume S | 15.0 |
| Sodium lauryl sulphate | 6.0 |
| Propylene glycol | 34.0 |
| Ethylene glycol monophenyl ether | 10.0 |
| Caproyl trimethicone | 1.0 |
| Water to | 100.0 |

EXAMPLE 7

| | A | B |
|---|---|---|
| Perfume V | 4.0% | — |
| Perfume BB | — | 3.0% |
| Sodium n-cocoyl L-glutamate | 6.0% | 5.0% |
| Hexylene glycol | 10.0% | 10.0% |
| Propylene glycol | 10.0% | 10.0% |
| Ethylene glycol monophenyl ether | 10.0% | 10.0% |
| Water to | 100.0% | 100.0% |

EXAMPLE 8

| | A | B | C |
|---|---|---|---|
| Perfume SA | 10.0 | 10.0% | 15.0% |
| Sodium n-cocoyl L-glutamate | 7.0% | 3.0% | 7.0% |
| Sodium lauryl sulfate | — | 3.0% | — |
| Hexylene glycol | 10.0% | 10.0% | 9.0% |
| Propylene glycol | 25.0% | 25.0% | 35.0% |
| Ethylene glycol monophenyl ether | 10.0% | 10.0% | 9.0% |
| Water to | 100.0% | 100.0% | 100.0% |

To demonstrate the spectrum of perfume types that this microemulsion system can accommodate, model technical perfume blends were created as examples of (1) relatively water soluble mixtures and (2) relatively water insoluble mixtures.

| Water Soluble Mixture (WS) | |
|---|---|
| Diethyl malonate | 20% |
| Linalool oxide | 20% |
| Octahydro coumarin | 20% |
| Phenyl ethanol | 20% |
| Vanillin | 20% |

| Water Insoluble Mixture (WI) | |
|---|---|
| Fixolide | 20% |
| Hexyl cinnamic aldehyde | 20% |
| Iso E Super | 20% |
| Lilial | 20% |
| d-Limonene | 20% |

EXAMPLE 9

| | A | B | C | D |
|---|---|---|---|---|
| WS Perfume | 5% | 5% | 15% | 15% |
| Sodium lauryl sulphate | 6% | 4% | 6% | 5% |
| Propylene glycol | 10% | 20% | 29% | 32% |
| Ethylene glycol monophenyl ether | — | 5% | — | 3% |
| Water to | 100% | 100% | 100% | 100% |

EXAMPLE 10

| | A | B |
|---|---|---|
| WI Perfume | 5.0% | 15.0% |
| Sodium lauryl sulphate | 6.0% | 5.0% |
| Propylene glycol | 7.5% | 25.0% |
| Ethylene glycol monophenyl ether | 7.5% | 20.0% |
| Water to | 100.0% | 100.0% |

Obviously, combinations of water soluble and water insoluble formulations may be produced.

EXAMPLE 11

| | A | B |
|---|---|---|
| WS/WI @ 1:1 | 5% | 15% |
| Sodium lauryl sulphate | 6% | 5% |
| Propylene glycol | 16% | 30% |
| Ethylene glycol monophenyl ether | 5% | 10% |
| Water to | 100% | 100% |

Each of the formulations in Examples 1–11 was tested for emulsion stability as follows. A sample of each formulation composition was subjected to at least three cycles of freezing and thawing. After thawing the sample for at least the third time, the stability of the sample was checked. Each sample was still in the form of a sprayable emulsion. Thus, the formulations as described in Examples 1–11 are stable sprayable emulsions. Additionally, the formulations were subjected to standard stability testing at 40° F. (4° C.) and 110° F. (43° C.) for 4 weeks.

The foregoing description has been provided for illustrative purposes. It will be recognized that variations on the inventive concepts disclosed herein may be envisioned which have not been specifically enumerated above. Such variations are nevertheless intended to be encompassed within the scope of the invention as set forth in the following claims.

We claim:

1. A low VOC, sprayable, non-sticky, non-ethanolic or low ethanolic, perfumery composition consisting essentially of a fragrance oil or a mixture of fragrance oils microemulsified by a combination of an anionic component (a) and at least one hydrophilic component (b), wherein
  (a) is an anionic surfactant or a combination of anionic surfactant, selected from the group consisting of acyl glutamates, alkyl sulphates, alkali metal sulphates, ammonium sulphates, substituted ammonium alkyl sulphates, alkyl ether sulphates having 10 to 30 carbon atoms in the alkyl moiety and 1 to 50 ethylene oxide units, sulphosuccinates, alkyl sulphonates, alkyl oxyalkane sulphonates, alkyl aryl sulphonates, alkanoic acid, alkanoates, sodium alkanoate soaps wherein the fatty acid moiety contains 10 to 20 carbon atoms, potassium alkanoate soaps wherein the fatty acid moiety contains 10 to 20 carbon atoms, triethanolamine soaps wherein the fatty acid moiety contains 10 to 20 carbon atoms, and acyl isothionates, or a combination thereof, said anionic surfactant being capable of forming a dispersion of said fragrance oil, or mixture of oils, and
  (b) is a highly water soluble, or infinitely water soluble, hydrophilic coactive solvent or mixture of hydrophilic coactive solvents, said hydrophilic coactive solvent or mixture being capable of sufficiently modifying the hydrophilic-lipophilic balance of said anionic surfactant or mixture of surfactant in said dispersion to enable formation of stable and clear, or near clear micro-emulsions of said fragrance oil or mixture of oils in water, said hydrophilic coactive solvent or at least one of said hydrophilic coactive solvents, being selected from the group consisting of short branched-chain or straight-chain aliphatic glycols, short branched-chain or straight-chain aliphatic ether alcohols, and ethoxylated polysiloxanes, or a combination thereof;

wherein said hydrophilic component (b) is present at a higher concentration by weight than said anionic component (a) in said perfumery composition; and wherein said fragrance oil or mixture of fragrance oils in combination with said components (a) and (b) in said perfumery composition are microemulsified to clarity or near clarity in an aqueous solvent.

2. The fragrance composition according to claim 1, wherein the fragrance component is an odiferous natural or synthetic material selected from the group consisting of oil soluble perfume oils, oil soluble perfume oils in a mixture with water soluble perfume oils, wherein the oil soluble perfume oils are:

(aa) natural, or nature-identical, essential oils selected from the group consisting of an orange oil, pine oil, peppermint oil, eucalyptus oil, lemon oil, clove leaf oil, cedarwood oil, bergamot oil, rosemary oil, patchouli oil, lavandin oil, spike oil, rose oil, vetiver oil, fennel oil, anise oil, thyme oil, germanium oil, lavender oil, menthol, or a combination thereof;

(bb) synthetic oil soluble perfume oils selected from the group consisting of hydrocarbons, alcohols, ketones, aldehydes, esters and polyene compounds, or a combination thereof; or (cc) a mixture of (aa) and (bb).

3. The fragrance composition according to claim 2, wherein said odiferous natural or synthetic material, is a natural or synthetic perfume oil, a mixture of perfume oils, or a perfume concentrate or base, in a non-ethanolic diluent or diluents.

4. The fragrance composition according to claim 2, wherein said anionic surfactants (a) are selected from the group consisting of monosodium cocoyl glutamate, $C_{9-8}$ alkyl sulphates, sodium lauryl sulphate, sodium laureth sulphate, sodium dioctyl sulphosuccinate, sodium $C_{12-14}$olefin sulphonate, sodium 2-methoxy-tridecane-sulphonate, sodium dodecyl benzene sulphonate, potassium oleate, sodium caprylate, and sodium cocoyl isothionate, or a combination thereof.

5. The fragrance composition according to claim 2, wherein the highly water soluble, or infinitely water soluble, hydrophilic coactive solvent or solvents (b) is selected from the group consisting of ethylene glycol, propylene glycol, butylene glycol, dipropylene glycol, hexylene glycol, isoprene glycol, methyl methoxy butanol, ethylene glycol butyl ether, propylene glycol methyl ether, and dimethicone copolyol, or a combination thereof.

6. The fragrance formulation according to claim 2, wherein the perfume materials are present at levels between 0.5% and 40% by weight of the composition.

7. The fragrance formulation according to claim 6, wherein the perfume materials are present at levels between 1% and 30% by weight of the composition.

8. The fragrance composition according to claim 2, wherein one or more anionic surfactants of component (a) is present in said composition at levels between about 1–40% by weight of the composition.

9. The fragrance composition according to claim 8, wherein one or more anionic surfactants of component (a) is present in said composition at levels between about 2–20% by weight of the composition.

10. The fragrance composition according to claim 1, wherein component (b) is one or more highly or infinitely water soluble components present in said composition at levels between about 1.5–55% by weight of the composition.

11. The fragrance composition according to claim 2, wherein component (b) is one or more highly or infinitely water soluble components present in said composition at levels between about 1.5–55% by weight of the composition.

12. The fragrance composition according to claim 2, wherein component (a) is present in said composition at levels between about 1–40% by weight of the composition, component (b) is present in said composition at levels between about 1.5–55% by weight of the composition, said fragrance component is present at levels between 0.5–50%, and the remainder of said composition by weight is water or a water/ethanol mixture wherein said ethanol when present is in low concentration.

13. The fragrance composition according to claim 12, wherein component (a) is present in said composition at levels between about 2–20% by weight of the composition, component (b) is present in said composition at levels between about 6–45% by weight of the composition, said fragrance component is present at levels between 1–30% by weight of the composition, and the remainder of said composition by weight is water or a water/ethanol mixture wherein said ethanol is present in a low concentration.

14. The fragrance composition according to claim 12, wherein component (a) is present in said composition at about 2% by weight of the composition, and said fragrance component is present at about 1% by weight of the composition.

15. The fragrance composition according to claim 14, wherein component (a) is present in said composition at about 7% by weight of the composition, and said fragrance component is present at about 40% by weight of the composition.

16. The fragrance composition according to claim 2, wherein the alkyl sulphate is sodium lauryl sulphate.

17. The fragrance composition according to claim 2, wherein the sulphosuccinate is sodium dioctyl sulphosuccinate.

18. The fragrance composition according to claim 2, wherein the acyl isothionate is sodium cocoyl isothionate.

19. The fragrance composition according to claim 2, wherein the alkanoate is sodium caprylate.

20. The fragrance composition according to claim 1, wherein the acyl glutamate is monosodium cocoyl glutamate.

21. The fragrance composition according to claim 1, wherein the short chain aliphatic glycol is selected form the group consisting of ethylene glycol, propylene glycol, butylene glycol, dipropylene glycol, hexylene glycol, isoprene glycol, or a combination thereof.

22. A low VOC, sprayable, non-sticky, non-ethanolic or low ethanolic, perfumery composition consisting essentially of a microemulsion of conventional perfumery materials, said composition having a fragrance oil or a mixture of fragrance oils solubilized by microemulsifying said oil or oils by a combination of an anionic component (a) and at least one hydrophilic component (b), wherein (a) is an anionic surfactant, or a combination of anionic surfactant, selected from the group consisting of acyl glutamates, alkyl sulphates, alkali metal sulphates, ammonium sulphates, substituted ammonium alkyl sulphates, alkyl ether sulphates having 10 to 30 carbon atoms in the alkyl moiety and 1 to 50 ethylene oxide units, sulphosuccinates, alkyl sulphonates, alkyl oxyalkane sulphonates, alkyl aryl sulphonates, alkanoic acid, alkanoates, sodium alkanoate soaps wherein the fatty acid moiety contains 10 to 20 carbon atoms, potassium alkanoate soaps wherein the fatty acid moiety contains 10 to 20 carbon atoms, triethanolamine soaps wherein the fatty acid moiety contains 10 to 20 carbon atoms, and acyl isothionates, or a combination thereof, said anionic surfactant being capable of forming a dispersion of said fragrance oil, or mixture of oils, and (b) is a mixture of components (i) and (ii), wherein (i) is a highly water soluble solvent selected from the group consisting of short branched-chain or straight-chain aliphatic glycols, short branched-chain or straight-chain aliphatic ether alcohols, and ethoxylated polysiloxanes, or a combination thereof; and (ii) is a polar water soluble solvent selected from the group consisting of short branched-chain or straight-chain aliphatic alcohols, unsubstituted aromatic alcohols, aromatic alcohols substituted by a branched-chain or straight-chained alkyl group, aromatic ether alcohols, and dimethyl silicones terminated with hydroxyl groups, or a combination thereof;

said mixture of (i) and (ii) being capable of sufficiently modifying the hydrophilic- lipophilic balance of said anionic surfactant, or mixture of surfactant, in said dispersion to enable formation of stable and clear, or near clear, microemulsions of said fragrance oil, or mixture of oils, in water;

wherein said hydrophilic component mixture (b) is present at a higher concentration by weight than said anionic component (a) in said perfumery composition; and wherein said fragrance oil or mixture of fragrance oils in combination with said components (a) and (b) in said perfumery composition are microemulsified to clarity, or near clarity, in an aqueous solvent.

* * * * *